(12) United States Patent
Nielsen et al.

(10) Patent No.: US 7,348,470 B2
(45) Date of Patent: *Mar. 25, 2008

(54) TRANSGENIC PLANT EXPRESSING MALTOGENIC ALPHA-AMYLASE

(76) Inventors: Jack Bech Nielsen, Ole Olsens Alle 12, Hellerup (DK) DK-2900; Soren Kjaerulff, Kongsdalsvej 47, Vanlose (DK) DK-2720

(*) Notice: Subject to any disclaimer, the term of this patent is extended or adjusted under 35 U.S.C. 154(b) by 349 days.

This patent is subject to a terminal disclaimer.

(21) Appl. No.: 11/048,000

(22) Filed: Jan. 31, 2005

(65) Prior Publication Data

US 2005/0144668 A1 Jun. 30, 2005

Related U.S. Application Data

(63) Continuation of application No. 09/831,656, filed as application No. PCT/DK99/00624 on Nov. 12, 1999, now Pat. No. 6,940,002.

(60) Provisional application No. 60/123,643, filed on Mar. 10, 1999.

(30) Foreign Application Priority Data

Nov. 12, 1998 (DK) .............................. 1998 01478

(51) Int. Cl.
*A01H 5/00* (2006.01)
*A01H 5/10* (2006.01)
*C12H 15/52* (2006.01)
*C12N 15/56* (2006.01)
*C12N 15/82* (2006.01)

(52) U.S. Cl. ...................... 800/284; 800/278; 800/320; 800/320.3; 435/419; 435/435

(58) Field of Classification Search ................ 800/278, 800/284, 320, 320.3; 536/23.1, 23.2, 23.7; 435/204, 419, 430
See application file for complete search history.

(56) References Cited

U.S. PATENT DOCUMENTS 6,940,002 B1 * 9/2005 Nielsen et al. .............. 800/284

FOREIGN PATENT DOCUMENTS

| EP | 0 120 693 | 10/1984 |
|---|---|---|
| EP | 0 479 359 A1 | 4/1992 |
| EP | 0 781 849 A1 | 7/1997 |
| WO | WO 91/04669 | 4/1991 |
| WO | WO 91/14772 | 10/1991 |
| WO | WO 92/01042 | 1/1992 |
| WO | WO 97/32986 | 9/1997 |
| WO | WO 98/18332 | 5/1998 |
| WO | WO 99/43793 | 9/1999 |
| WO | WO 99/43794 | 9/1999 |
| WO | WO 00/08185 | 2/2000 |

OTHER PUBLICATIONS

Nielsen J. et al. Protein Engineering, 2001; vol. 14, No. 7; pp. 505-512.*
Guinto, E R. et al. PNAS, USA vol. 96, pp. 1852-1857, Mar. 1999.*
Diderichsen et al., "Cloning of maltogenic alpha-amylase from *Bacillus sterarothermophilus*"; FEMS Microbiol. Lett. 56: 53-60 (1988).
Barro et al., "Transformation of wheat with high molecular weight subunit genes results in improved functional properties", Nature Biotechnology, vol. 15, Nov. 1997.
Vickers et al., "Assessment of *Bacillus licheniformis* alpha-amylase as Candidate Enzyme For Genetic Engineering of Malting Barley", J. Inst. Brew., Mar.-Apr. 1996, vol. , pp. 75-78.
Christophersen et al., "Enzymatic Characterization of Novamyl a Thermostable alpha-amylase", Starch 50 (1988) Nr. 1, S. 39-45.

* cited by examiner

*Primary Examiner*—Russell P. Kallis

(57) ABSTRACT

A transgenic plant cell expressing a maltogenic amylase (such as Novamyl®) or a beta-amylase; a transgenic plant regenerated from said cell; seeds generated from such plant where said seeds comprise a maltogenic amylase or a beta-amylase and the use of said seeds, optionally in ground form, for catalyzing an industrial process, such as e.g. in baking. The maltogenic amylase providing an anti staling effect in bread produced from the seeds in question.

21 Claims, No Drawings

SEQUENCE LISTING

<160> NUMBER OF SEQ ID NOS: 4

<210> SEQ ID NO 1
<211> LENGTH: 2160
<212> TYPE: DNA
<213> ORGANISM: Bacillus sp.

<400> SEQUENCE: 1

| | | | | | |
|---|---|---|---|---|---|
| atgaaaaga | aaacgctttc | tttatttgtg | ggactgatgc | tcctcatcgg | tcttctgttc | 60 |
| agcggttctc | ttccgtacaa | tccaaacgcc | gctgaagcca | gcagttccgc | aagcgtcaaa | 120 |
| ggggacgtga | tttaccagat | tatcattgac | cggttttacg | atggggacac | gacgaacaac | 180 |
| aatcctgcca | aaagttatgg | actttacgat | ccgaccaaat | cgaagtggaa | aatgtattgg | 240 |

```
ggcggggatc tggaggggggt tcgtcaaaaa cttccttatc ttaaacagct gggcgtaacg    300
acaatctggt tgtccccggt tttggacaat ctggatacac tggcgggcac cgataacacg    360
ggctatcacg gatactggac gcgcgatttt aaacagattg aggaacattt cgggaattgg    420
accacatttg acacgttggt caatgatgct caccaaaacg gaatcaaggt gattgtcgac    480
tttgtgccca atcattcgac tccttttaag gcaaacgatt ccacctttgc ggaaggcggc    540
gccctctaca acaatggaac ctatatgggc aattattttg atgacgcaac aaaagggtac    600
ttccaccata tggggacat cagcaactgg gacgaccggt acgaggcgca atggaaaaac    660
ttcacggatc cagccggttt ctcgcttgcc gatttgtcgc aggaaaatgg cacgattgct    720
caatacctga ccgatgcggc ggttcaattg gtagcacatg gagcggatgg tttgcggatt    780
gatgcggtga agcattttaa ttcggggttc tccaaatcgt tggccgataa actgtaccaa    840
aagaaagaca ttttcctggt gggggaatgg tacgagatg accccggaac agccaatcat    900
ctggaaaagg tccggtacgc caacaacagc ggtgtcaatg tgctggattt tgatctcaac    960
acggtgattc gaaatgtgtt cggcacattt acgcaaacga tgtacgatct taacaatatg   1020
gtgaaccaaa cggggaacga gtacaaatac aaagaaaatc taatcacatt tatcgataac   1080
catgatatgt caagatttct ttcggtaaat tcgaacaagg cgaatttgca ccaggcgctt   1140
gctttcattc tcacttcgcg gggtacgccc tccatctatt atggaaccga acaatacatg   1200
gcaggcggca atgacccgta caaccggggg atgatgccgg cgtttgatac gacaaccacc   1260 gccttttaaag aggtgtcaac tctggcgggg ttgcgcagga caatgcggc gatccagtac   1320 ggcaccacca cccagcgttg gatcaacaat gatgtttaca tttatgaacg gaaattttc   1380 aacgatgtcg tgttggtggc catcaatcga aacacgcaat cctcctattc gatttccggt   1440
ttgcagacgg ccttgccaaa tggcagctat gcggattatc tgtcagggct gttggggggg   1500
aacgggattt ccgtttccaa tggaagtgtc gcttcgttca cgcttgcgcc tggagccgtg   1560
tctgtttggc agtacagcac atccgcttca gcgccgcaaa tcggatcggt tgctccaaat   1620
atggggattc cgggtaatgt ggtcacgatc gacgggaaag gttttgggac gacgcaggga   1680
accgtgacat ttggcggagt gacagcgact gtgaaatcct ggacatccaa tcggattgaa   1740
gtgtacgttc caacatggc cgccgggctg accgatgtga agtcaccgc gggtggagtt   1800 tccagcaatc tgtattctta caatattttg agtggaacgc agacatcggt tgtgtttact   1860
gtgaaaagtg cgcctccgac caacctgggg gataagattt acctgacggg caacataccg   1920
gaattgggga attggagcac ggatacgagc ggagccgtta caatgcgca agggccctg   1980 ctcgcgccca attatccgga ttggttttat gtattcagcg ttccagcagg aaagacgatt   2040
caattcaagt tcttcatcaa gcgtgcggat ggaacgattc aatgggagaa tggttcgaac   2100
cacgtggcca aactcccac gggtgcaacc ggtaacatta ctgttacgtg gcaaaactag   2160
```

<210> SEQ ID NO 2
<211> LENGTH: 719
<212> TYPE: PRT
<213> ORGANISM: Bacillus sp

<400> SEQUENCE: 2

Met Lys Lys Lys Thr Leu Ser Leu Phe Val Gly Leu Met Leu Leu Ile
1               5                   10                  15

Gly Leu Leu Phe Ser Gly Ser Leu Pro Tyr Asn Pro Asn Ala Ala Glu
            20                  25                  30

-continued

```
Ala Ser Ser Ser Ala Ser Val Lys Gly Asp Val Ile Tyr Gln Ile Ile
        35                  40                  45

Ile Asp Arg Phe Tyr Asp Gly Asp Thr Thr Asn Asn Asn Pro Ala Lys
    50                  55                  60

Ser Tyr Gly Leu Tyr Asp Pro Thr Lys Ser Lys Trp Lys Met Tyr Trp
65                  70                  75                  80

Gly Gly Asp Leu Glu Gly Val Arg Gln Lys Leu Pro Tyr Leu Lys Gln
                85                  90                  95

Leu Gly Val Thr Thr Ile Trp Leu Ser Pro Val Leu Asp Asn Leu Asp
            100                 105                 110

Thr Leu Ala Gly Thr Asp Asn Thr Gly Tyr His Gly Tyr Trp Thr Arg
        115                 120                 125

Asp Phe Lys Gln Ile Glu Glu His Phe Gly Asn Trp Thr Thr Phe Asp
    130                 135                 140

Thr Leu Val Asn Asp Ala His Gln Asn Gly Ile Lys Val Ile Val Asp
145                 150                 155                 160

Phe Val Pro Asn His Ser Thr Pro Phe Lys Ala Asn Asp Ser Thr Phe
                165                 170                 175

Ala Glu Gly Gly Ala Leu Tyr Asn Asn Gly Thr Tyr Met Gly Asn Tyr
            180                 185                 190

Phe Asp Asp Ala Thr Lys Gly Tyr Phe His His Asn Gly Asp Ile Ser
        195                 200                 205

Asn Trp Asp Asp Arg Tyr Glu Ala Gln Trp Lys Asn Phe Thr Asp Pro
    210                 215                 220

Ala Gly Phe Ser Leu Ala Asp Leu Ser Gln Glu Asn Gly Thr Ile Ala
225                 230                 235                 240

Gln Tyr Leu Thr Asp Ala Val Gln Leu Val Ala His Gly Ala Asp
                245                 250                 255

Gly Leu Arg Ile Asp Ala Val Lys His Phe Asn Ser Gly Phe Ser Lys
            260                 265                 270

Ser Leu Ala Asp Lys Leu Tyr Gln Lys Lys Asp Ile Phe Leu Val Gly
        275                 280                 285

Glu Trp Tyr Gly Asp Asp Pro Gly Thr Ala Asn His Leu Glu Lys Val
    290                 295                 300

Arg Tyr Ala Asn Asn Ser Gly Val Asn Val Leu Asp Phe Asp Leu Asn
305                 310                 315                 320

Thr Val Ile Arg Asn Val Phe Gly Thr Phe Thr Gln Thr Met Tyr Asp
                325                 330                 335

Leu Asn Asn Met Val Asn Gln Thr Gly Asn Glu Tyr Lys Tyr Lys Glu
            340                 345                 350

Asn Leu Ile Thr Phe Ile Asp Asn His Asp Met Ser Arg Phe Leu Ser
        355                 360                 365

Val Asn Ser Asn Lys Ala Asn Leu His Gln Ala Leu Ala Phe Ile Leu
    370                 375                 380

Thr Ser Arg Gly Thr Pro Ser Ile Tyr Tyr Gly Thr Glu Gln Tyr Met
385                 390                 395                 400

Ala Gly Gly Asn Asp Pro Tyr Asn Arg Gly Met Met Pro Ala Phe Asp
                405                 410                 415

Thr Thr Thr Thr Ala Phe Lys Glu Val Ser Thr Leu Ala Gly Leu Arg
            420                 425                 430

Arg Asn Asn Ala Ala Ile Gln Tyr Gly Thr Thr Thr Gln Arg Trp Ile
        435                 440                 445

Asn Asn Asp Val Tyr Ile Tyr Glu Arg Lys Phe Phe Asn Asp Val Val
```

```
                450                 455                 460
Leu Val Ala Ile Asn Arg Asn Thr Gln Ser Ser Tyr Ser Ile Ser Gly
465                 470                 475                 480

Leu Gln Thr Ala Leu Pro Asn Gly Ser Tyr Ala Asp Tyr Leu Ser Gly
                485                 490                 495

Leu Leu Gly Gly Asn Gly Ile Ser Val Ser Asn Gly Ser Val Ala Ser
                500                 505                 510

Phe Thr Leu Ala Pro Gly Ala Val Ser Val Trp Gln Tyr Ser Thr Ser
                515                 520                 525

Ala Ser Ala Pro Gln Ile Gly Ser Val Ala Pro Asn Met Gly Ile Pro
                530                 535                 540

Gly Asn Val Val Thr Ile Asp Gly Lys Gly Phe Gly Thr Thr Gln Gly
545                 550                 555                 560

Thr Val Thr Phe Gly Gly Val Thr Ala Thr Val Lys Ser Trp Thr Ser
                565                 570                 575

Asn Arg Ile Glu Val Tyr Val Pro Asn Met Ala Ala Gly Leu Thr Asp
                580                 585                 590

Val Lys Val Thr Ala Gly Gly Val Ser Ser Asn Leu Tyr Ser Tyr Asn
                595                 600                 605

Ile Leu Ser Gly Thr Gln Thr Ser Val Val Phe Thr Val Lys Ser Ala
610                 615                 620

Pro Pro Thr Asn Leu Gly Asp Lys Ile Tyr Leu Thr Gly Asn Ile Pro
625                 630                 635                 640

Glu Leu Gly Asn Trp Ser Thr Asp Thr Ser Gly Ala Val Asn Asn Ala
                645                 650                 655

Gln Gly Pro Leu Leu Ala Pro Asn Tyr Pro Asp Trp Phe Tyr Val Phe
                660                 665                 670

Ser Val Pro Ala Gly Lys Thr Ile Gln Phe Lys Phe Phe Ile Lys Arg
                675                 680                 685

Ala Asp Gly Thr Ile Gln Trp Glu Asn Gly Ser Asn His Val Ala Thr
                690                 695                 700

Thr Pro Thr Gly Ala Thr Gly Asn Ile Thr Val Thr Trp Gln Asn
705                 710                 715

<210> SEQ ID NO 3
<211> LENGTH: 33
<212> TYPE: DNA
<213> ORGANISM: Artificial Sequence
<220> FEATURE:
<223> OTHER INFORMATION: FNP 110

<400> SEQUENCE: 3
tcccccggga tgagcagttc cgcaagcgtc aaa                              33

<210> SEQ ID NO 4
<211> LENGTH: 25
<212> TYPE: DNA
<213> ORGANISM: Artificial Sequence
<220> FEATURE:
<223> OTHER INFORMATION: RNP 110

<400> SEQUENCE: 4
cgatgagctc ctagttttgc cacgt                                       25
```

TRANSGENIC PLANT EXPRESSING MALTOGENIC ALPHA-AMYLASE

CROSS-REFERENCE TO RELATED APPLICATIONS

This application is a continuation of U.S. application Ser. No. 09/831,656, filed Sep. 2, 2001 now U.S. Pat. No. 6,940,002, which is a 35 U.S.C. 371 national application of PCT/DK99/00624 filed Nov. 12, 1999, which claims priority or the benefit under 35 U.S.C. 119 of Danish application no. PA 1998 01478, filed Nov. 12, 1998 and U.S. provisional application No. 60/123,643 filed Mar. 10, 1999, the contents of which are fully incorporated herein by reference.

FIELD OF THE INVENTION

The present invention relates to a transgenic plant cell expressing a maltogenic amylase or a beta-amylase, a transgenic plant regenerated from said cell, seeds comprising a maltogenic amylase or a beta-amylase and the use of said seeds, optionally in ground form, for catalyzing an industrial process.

BACKGROUND OF THE INVENTION

Maltogenic alpha-amylase (glucan 1,4-α-maltohydrolase, E.C. 3.2.1.133) is able to hydrolyze amylose and amylopectin to maltose in the alpha-configuration, and is also able to hydrolyze maltotriose as well as cyclodextrin. A maltogenic alpha-amylase from *Bacillus* (EP 120 693) is commercially available under the trade name Novamyl® (product of Novo Nordisk A/S, Denmark) and is widely used in the baking industry as an anti-staling agent due to its ability to reduce retrogradation of starch/amylopectin. Novamyl is further described by Christophersen, C., et al., 1998, Starch 50, pp 39-45. Variants of Novamyl® and the three-dimensional structure of Novamyl® are disclosed in WO 99/43794.

WO 91/14772 discloses transgenic seeds expressing enhanced amounts of enzymes, and the use of such seeds in catalyzing industrial processes. Baking is mentioned as one example of an industrial process for which α-amylase can be used and it is stated that the seeds may be ground before being incorporated into flour.

Vickers et al, Journal of the Institute of Brewing, Vol. 102, No. 2 pp. 75-78 (1996) speculate in using a *Bacillus licheniformis* α-amylase as a candidate enzyme for the genetic transformation of malting barley.

BRIEF DESCRIPTION OF THE INVENTION

The present invention relates to a cell of a transgenic seed producing plant transformed with at least one nucleotide sequence encoding a maltogenic alpha-amylase or a beta-amylase which, in the cell, is operably linked to elements required for mediating expression from said nucleotide sequence in the seeds of a plant regenerated from the plant cell.

In a further aspect the invention relates to a transgenic seed-producing plant regenerated from a cell of the invention and expressing measurable quantities of a maltogenic alpha-amylase or a beta-amylase in its seeds.

In a still further aspect the invention relates to the seeds of a plant of the invention, optionally in ground form, and the use of such seed for catalyzing an industrial process.

The invention also relates to a method for producing a maltogenic alpha-amylase or beta-amylase comprising recovering the amylase or the beta-amylase from seeds of the invention.

DETAILED DISCLOSURE OF THE INVENTION

The maltogenic alpha-amylase is an enzyme classified in EC 3.2.1.133. The enzymatic activity does not require a non-reducing end on the substrate and the primary enzymatic activity results in the degradation of amylopectin and amylose to maltose and longer maltodextrins. It is able to hydrolyze amylose and amylopectin to maltose in the alpha-configuration, and is also able to hydrolyze maltotriose as well as cyclodextrin.

For the present invention in a particularly interesting embodiment the maltogenic alpha-amylase enzyme corresponds to maltogenic alpha-amylase cloned from *Bacillus* as described in EP 120 693 (hereinafter referred to as Novamyl). Novamyl has the amino acid sequence set forth in amino acids 1-686 of SEQ ID NO: 1. Novamyl is encoded in the gene harboured in the *Bacillus* strain NCIB 11837 (c.f. EP 120 693) which has the nucleic acid sequence set forth in SEQ ID NO:1. Thus, in one preferred embodiment of the invention the maltogenic alpha-amylase enzyme is identical to a maltogenic alpha-amylase obtainable from *Bacillus* strain NCIB 11837. In the context of the invention is also contemplated a nucleotide sequence encoding said enzyme, such as e.g. a nucleotide sequence obtainable from *Bacillus* strain NCIB 11837 encoding said enzyme. The coding sequence for Novamyl may be obtained from the strain DSM 11837 or from the plasmid denoted pLBei010 as indicated in WO 99/43794. The plasmid pLBei010 contains amyM in which the expression of amyM is directed by its own promoter and the complete gene encoding Novamyl, e.g., as contained in the strain DSM 11837. The plasmid contains the origin of replication, ori, from plasmid pUB110 and an kanamycin resistance marker for selection purposes. pLBei010 is shown in FIG. 1. Preferably the maltogenic alpha-amylase enzyme for the present invention has an anti-staling effect in baking.

The present inventors have found that maltogenic alpha-amylases, (such as, e.g. Novamyl®) has a very unique performance in bread making. Other thermostable α-amylases like BAN® (product of Novo Nordisk A/S) or Termamyl® (product of Novo Nordisk A/S) must be dosed very carefully in tight intervals, e.g. between 0.5-2 times of the optimum dosage in a given recipe. Otherwise the risk is high that there is either no effect (low dosage) or too high effect (high dosage). The latter results in a gummy, non-elastic and sticky crumb, unsuited for eating. The inventors have found that maltogenic alpha-amylases does not have this problem, but can be dosed broadly. For instance, Novamyl® has a positive function on e.g. staling properties from a level of e.g. 200 MANU/kg flour to 5.000 MANU/kg, i.e. a much safer amylase in practical application than other α-amylases. This property of Novamyl® is thus a fundamental difference compared to known α-amylases. This characteristic makes it superior in baking applications, such as in connection with anti-staling, and it is also contemplated that this property makes maltogenic alpha-amylases, such as e.g. Novamyl®, particularly suitable for transgenic expression in plants, in particular in a seed producing plant, such as e.g. wheat. Accordingly, one embodiment of the present invention relates to the expression of a maltogenic alpha-amylase, such as Novamyl, in the seeds of a seed producing plant, such as, e.g. wheat.

Of particular interest for the present invention is enzymes having an anti-staling effect and at the same time having the above indicated characteristic, i.e. that relatively high dosage of the enzyme in baking does not have an essentially negative effect as compared to other enzymes. Within the scope of the invention is expression of such enzymes (with anti-staling effect and the above indicated dosage characteristics in baking) in the seeds of a seed producing plant, such as, e.g. wheat, and the use of such seed in baking. Examples of enzymes with such characteristics are maltogenic alpha-amylases, such as Novamyl. The negative effect of high dosage may be exemplified by the effect of use of high dosage of α-amylases in baking as indicated above.

Beta-amylase is another example of an enzyme that shows a relatively low level of criticality to high dosage in baking. Thus, one embodiment of the present invention relates to the expression of a beta-amylase in the seeds of a seed producing plant, such as, e.g. wheat, and the use of such seed in baking.

Within the scope of the invention is a maltogenic alpha-amylase being this an enzyme with one or more characteristics selected from the group consisting of:
i) having the amino acid sequence set forth in SEQ ID NO:2;
ii) having the amino acid sequence set forth in amino acids 1-686 of SEQ ID NO:1;
iii) having a three dimensional structural homology to Novamyl;
iv) having an amino acid sequence which has at least 70% identity to SEQ ID NO: 2, preferably at least 75%, 80%, 85% or at least 90%, e.g. at least 95%, 97%, 98%, or at least 99%;
v) having an amino acid sequence which has at least 70% identity to the amino acid sequence set forth in amino acids 1-686 of SEQ ID NO:1, preferably at least 75%, 80%, 85% or at least 90%, e.g. at least 95%, 97%, 98%, or at least 99%;
vi) a fragment of i), ii) iv) or v), said fragment consisting of 10-600 amino acid residues, such as in the range of 30-300 amino acid residues, such as 50-100 amino acid residues;
vii) an amino acid sequence encoded by a nucleotide sequence which hybridizes (1) to the DNA sequence set forth in SEQ ID NO:1, (2) to the DNA sequence encoding Novamyl harboured in the *Bacillus* strain NCIB 11837, (3) to the DNA sequence contained in the nucleotides 100 to 2157 of SEQ ID NO:1, (4) to a subsequence of (1) or (3) of at least 30 nucleotides, such as at least 50 nucleotides, at least 100 nucleotides, at least 200 nucleotides, or (5) to a complementary strand of (1), (3), or (4) under low stringency conditions, or under medium stringency, more preferably at medium/high stringency or at high stringency or even more preferably at very high stringency;
viii) a catalytic binding site comprising amino acid residues similar to D229, E257 and D328 as shown in the amino acid sequence set forth in amino acids 1-686 of SEQ ID NO:1;
ix) a variant of the amino acid sequence set forth in amino acids 1-686 of SEQ ID NO:1 comprising a substitution, deletion, and/or insertion of one or more amino acids;

The structural homology referred to above in iii) is as disclosed in WO 99/43794 and is based on other sequence homologies, hydrophobic cluster analysis or by reverse threading (Huber, T; Torda, A E, PROTEIN SCIENCE Vol. 7, No. 1 pp. 142-149 (1998)) and which by any of these methods is predicted to have the same tertiary structure as Novamyl, wherein the tertiary structure refers to the overall folding or the folding of Domains A, B, and C, more preferably including Domain D, and most preferably including Domain E as disclosed in WO 99/43794. Alternatively, a structural alignment between Novamyl and a maltogenic alpha-amylase may be used to identify equivalent positions.

Maltogenic alpha-amylase variants are described in WO 99/43794. In further embodiments of the present invention the maltogenic alpha-amylase enzyme is a variant of the amino acid sequence set forth in amino acids 1-686 of SEQ ID NO:1 or a variant of SEQ ID NO:2, such variants are disclosed in WO 99/43794. WO 99/43794 also discloses how such suitable modifications may be identified and how to prepare the modifications. Accordingly, the maltogenic alpha-amylase enzyme of the invention may be a maltogenic alpha-amylase enzyme variant having a modified amino acid sequence compared the amino acid sequence set forth in amino acids 1-686 of SEQ ID NO:1 or compared to SEQ ID NO:2.

The maltogenic alpha-amylase enzyme variant may have one or more of the following properties which are modified compared to an enzyme having the amino acid sequence of set forth in amino acids 1-686 of SEQ ID NO:1 or compared to SEQ ID NO: 2, such as stability (e.g. thermostability), pH dependent activity, substrate specificity, specific activity or ability to reduce retrogradation of starch or staling of bread. Thus, the altered property may be an altered specific activity at a given pH and/or an altered substrate specificity, such as an altered pattern of substrate cleavage or an altered pattern of substrate inhibition.

These variants may be modifications of SEQ ID NO: 2 or the amino acid sequence set forth in amino acids 1-686 of SEQ ID NO:1 consisting in substitution, deletion or insertion, or a mixture of these, of one or more amino acid residues.

In further embodiments of the invention the variant of a maltogenic alpha-amylase has an altered pH dependent activity profile as compared to Novamyl and has an amino acid sequence comprising a modification of an amino acid residue corresponding to one or more of the following residues of the amino acid sequence set forth in SEQ ID NO: 1: D127, V129, F188, A229, Y258, V281, F284, T288, N327, M330, G370, N371, and D372, L71, S72, V74, L75, L78, T80, L81, G83, T84, D85, N86, T87, G88, Y89, H90, G91, T94, R95, D96, F97, I174, S175, N176, D178, D179, R180, Y181, E182, A183, Q184, K186, N187, F188, T189, D190, A192, G193, F194, S195, L196.

In further embodiments of the present invention the variant comprises a modification corresponding to one or more of the following modifications in the amino acid sequence set forth in SEQ ID NO: 1: D127N/L, V129S/T/G/V, F188E/K/H, A229S/T/V, Y258E/D/K/R/F/N, V281L/T, F284K/H/D/E/Y, T288E/K/R, N327D, M330L/F/I/D/E/K, G370N, N371D/E/G/K, and D372N/V, L71I, S72C, V74I, L75N/D/Q/I/V, L78N/I, T80I/L/V/S/N/G, L81I/V/S/T/N/Q/K/H, G83A/S/T/N/Q/E/D/R/H/L, T84S/A/N/D/G, D85A/T/S/N/G, N86Q/E/D/Y/H/K, T87S/I, G88A/S/T, Y89F, H90N/Q/K, G91A/S/T, T94N/D/A/M/V/I, R95K/Q, D96N/V/Q/I, F97Y, I174N/Q/L, S175T/A/N/D, N176S/T/H/Q/P, D178N/Q/E/K/H, D179Y/N/H, R180W, Y181R/F/C/L, E182D, A183S/C/G, Q184E, K186R, N187Q/E/L/F/H/K/V/L, F188Y/L/I/H/N, T189N/D/A/S/H/Y/G, D190E/Q/H/N/K, A192T/D/E/N/K, G193A/S/T, F194Y, S195N/D/E/R/K/G, L196I.

Other variants contemplated for the present invention are variants of Novamyl having an altered $Ca^{2+}$ binding as compared to the parent maltogenic alpha-amylase and where said variant has an amino acid sequence comprising a modification of an amino acid residue corresponding to one or more of the following residues of the amino acid sequence set forth in SEQ ID NO: 1: D17, A30, S32, R95, H103, N131, Q201, I174, and/or H169, V74, L75, L78, T80, L81,T87, G88, Y89, H90, G91, T94, R95, D96, F97, Y167, F168, H169, H170, N171, G172, D173, I174, S175, N176, D178, D179, R180, Y181, E182, A183, Q184, K186, N187, F188, T189.

In one embodiment, the variant of SEQ ID NO: 1 has an altered $Ca^{2+}$ binding as compared to the parent maltogenic alpha-amylase. In one embodiment of the invention the $Ca^{2+}$ binding of a maltogenic alpha-amylase is change the partial sequence N28-P29-A30-K31-S32-Y33-G34 as set forth in SEQ ID NO: 1 is modified.

Further contemplated variants are variants having an amino acid sequence comprising a substitution corresponding to one or more of the following substitutions in the amino acid sequence set forth in SEQ ID NO: 1: D17E/Q, A30M/L/A/V/I/E/Q, S32D/E/N/Q, R95M/L/A/V/I/E/Q, H103Y/N/Q/D/E, N131D, Q201E, I174E/Q, and H169N/D/E/Q, V74I, L75N/D/Q/I/V, L78N/I, T80I/L/V/S/N/G, L81I/V/S/T/N/Q/K/H, T87S/I, G88A/S/T, Y89F, H90N/Q/K, G91A/S/T, T94N/D/A/M/V/I, R95K/Q, D96N/V/Q/I, F97Y, Y167F/R/C, F168Y, H169N/Q/K, H170N/Q/K, N171D/E//Q/H/R/K/G, G172A/T/S, D173N/S/T/Y/R/G, I174N/Q/L, S175T/A/N/D, N176S/T/H//Q/P, D178N/Q/E/K/H, D179Y/N/H, R180W, Y181R/F/C/L, E182D, A183S/C/G, Q184E, K186R, N187Q/E/L/F/H/K/V/L, F188Y/L/I/H/N, T189N/D/A/S/H/Y/G.

The maltogenic alpha-amylase variants may also have an altered thermostability and/or an altered temperature dependent activity profile compared to Novamyl. Such variants may comprise a substitution of an amino acid residue corresponding to one or more of the following residues of the amino acid sequence set forth in SEQ ID NO: 1: L51, L75, L78, G88, G91, T94, V114, I125, V126, T134, G157, L217, S235, G236, V254, V279, V281, L286, V289, I290, V308, L321, I325, D326, L343, F349, S353, I359,I405, L448, Q449, L452, I470, G509, V515, S583, G625, L627, L628, and A670, L71, S72, V74, L75, L78, T80, L81, G83, T84, D85, N86, T87, G88, Y89, H90, G91, T94, R95, D96, F97, Y167, F168, H169, H170, N171, G172, D173, I174, S175, N176, D178, D179, R180, Y181, E182, A183, Q184, K186, N187, F188, T189, D190, A192, G193, F194, S195, L196.

Such variants in the context of the invention may comprise one or more substitutions corresponding to the following substitutions in the amino acid sequence set forth in SEQ ID NO: 1: L217 in combination with L75 (e.g. L217F/Y in combination with L75F/Y), L51W, L75F/Y, L78I, G88A/V/T, G91T/S/V/N, T94V/I/L, V114V/I/L, I125M/F/Y/W, V126I/L, T134V/I/L/M/F/Y/W, G157A/V/I/L, L217V/I/M/F/Y/W, S235I/L/M/F/Y/W, G236A/V/I/L/M/F/Y/W, V254I/L/M/F/Y/W, V279M/I/L/F, V281I/L/M/F/Y/W, L286F, V289I/L/R, I290M/L/F, V308I/L/M/F/Y/W, L321I/M/F/Y/W, I325L/M/F/Y/W, D326E/Q, L343M/F/Y/W, F349W/Y, S353V/I/L, I359L/M/F/Y/W, I405M/L/Y/F/W, L448Y, Q449Y, L452M/Y/F/W, I470M/L/F, G509A/V/I/L/M/S/T/D/N, V515I/L, S583V/I/L/V, G625A/V/I/L/M/F/Y/W, L627M/F/Y, L628M/I/F/Y/W and A670V/I/L/M/F/Y/W, L71I, S72C, V74I, L75N/D/Q/I/V, L78N/I, T80I/L/V/S/N/G, L81I/V/S/T/N/Q/K/H, G83A/S/T/N/Q/E/D/R/H/L, T84S/A/N/D/G, D85A/T/S/N/G, N86Q/E/D/Y/H/K, T87S/I, G88A/S/T, Y89F, H90N/Q/K, G91A/S/T, T94N/D/A/M/V/I, R95K/Q, D96N/V/Q/I, F97Y, Y167F/R/C, F168Y, H169N/Q/K, H170N/Q/K, N171D/E/Q/H/R/K/G, G172A/T/S, D173N/S/T/Y/R/G, I174N/Q/L, S175T/A/N/D, N176S/T/H/Q/P, D178N/Q/E/K/H, D179Y/N/H, R180W, Y181R/F/C/L, E182D, A183S/C/G, Q184E, K186R, N187Q/E/L/F/H/K/V/L, F188Y/L/I/H/N, T189N/D/A/S/H/Y/G, D190E/Q/H/N/K, A192D/E/N/K, G193A/S/T, F194Y, S195N/D/E/R/K/G, L196I.

Further variants may have an altered substrate binding site as compared to said parent. Such variant may comprise a modification in a position corresponding to one or both of the following positions in SEQ ID NO: 1: V281 and/or A629. In one embodiment of the invention the variant comprises a modification corresponding to: V281Q and/or A629N/D/E/Q.

Maltogenic alpha amylases having an improved ability to reduce the retrogradation of starch and/or the staling of bread compared to Novamyl is also contemplated within the context of the invention. Such variants of Novamyl may comprise a modification at one or more positions corresponding to the following amino acid residues in SEQ ID NO: 1: A30, K40, N115, T142, F188, T189, P191, A192, G193, F194, S195, D261, N237, K425, K520, and N595. Maltogenic alpha-amylases in the context of the invention may be a variant of Novamyl comprising one or more modifications corresponding to the following in SEQ ID NO: 1: A30D, K40R, N115D, T142A, F188L, T189Y, Δ (191-195), D261G, D261G, N327S, K425E, K520R and N595I.

Within the context of the invention are variants having a combination of one or more of the above with any of the other modifications disclosed herein.

Thus, the maltogenic alpha-amylase in relation to the present invention may have an amino acid which is modified compared to Novamyl where said modified sequence has one or more of the following modifications compared to the amino acid sequence set forth in amino acids 1-686 of SEQ ID NO:1: 192-A-193; Δ (191-195); D17E; S32Q; S32D; S32N; H103Y; N131D; I174Q; I174E; N176S; F188H; F188E; Δ 191; 192-A-193; 192-A-G-193; Δ 192; Δ 262-266; F284E; F284D; F284K; T288K; T288R; N327D; G397P; N115D+F188L; T142A+D261G; G370N+N371G; N115D+F188L; A30D+K40R+D261G; F188L+V336L+T525A; F188I+Y422F+I660V; F188L+D261G+T288P; Δ (191-195)+F188L+T189Y; K40R+F188L+D261G+A483T; T142A+N327S+K425E+K520R+N595I; T142A+N327S+K425E+K520R+N595I.

Nomenclature for amino acid modifications: The nomenclature used herein for defining mutations is essentially as described in WO 92/05249. Thus, F188H indicates a substitution of the amino acid F (Phe) in position 188 with the amino acid H (His). V129S/T/GN indicates a substitution of V129 with S, T, G or V. Δ (191-195) or A (191-195) indicates a deletion of amino acids in positions 191-195. 192-A-193 indicates an insertion of A between amino acids 192 and 193.

The polypeptide sequence identity referred to above in v) is determined as the degree of homology between two sequences indicating a derivation of the first sequence from the second. The identity may be suitably determined by means of computer programs known in the art such as GAP, provided in the GCG program package (Program Manual for the Wisconsin Package, Version 8, August 1994, Genetics Computer Group, 575 Science Drive, Madison, Wis., USA 53711; Needleman, S. B. and Wunsch, C. D., 1970, Journal of Molecular Biology, 48, 443-453). Using GAP with the following settings for polypeptide sequence comparison: GAP creation penalty of 3.0 and GAP extension penalty of 0.1, the mature protein part of a polypeptide encoded by an analogous DNA sequence of the invention exhibits a degree of identity preferably of at least 40%, preferably at least 50%, least 60%, at least 67%, at least 70%, preferably at least 75%, 80%, 85%, at least 90%, e.g. at least 95%, 97%, 98%, or at least 99% identity to the amino acid sequence set forth in amino acids 1-686 of SEQ ID NO:1 or to the amino acid sequence set forth in SEQ ID NO:2. In a prefered embodiment of the invention, the degree of identity between two amino acid sequences as disclosed herein is determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5].

In connection with maltogenic alpha-amylases characterised by vii), the oligonucleotide probe used in a hybridization may be suitably prepared on the basis of the nucleic acid sequence set forth in SEQ ID NO:1.

The hybridization referred to above in vii) is intended to indicate that the analogous DNA sequence hybridizes to the nucleotide probe corresponding to the protein encoding part of the nucleic sequence shown in SEQ ID NO:1, under at least low stringency conditions as described in detail below.

Suitable experimental conditions for determining hybridization at low stringency between a nucleotide probe and a homologous DNA or RNA sequence involves presoaking of the filter containing the DNA fragments or RNA to hybridize in 5×SSC (sodium chloride/sodium citrate, Sambrook, et al., 1989) for 10 min, and prehybridization of the filter in a solution of 5×SSC, 5× Denhardt's solution (Sambrook, et al., 1989), 0.5% SDS and 100 µg/ml of denatured sonicated salmon sperm DNA (Sambrook, et al., 1989), followed by hybridization in the same solution containing a random-primed (Feinberg, A. P. and Vogelstein, B. (1983) *Anal. Biochem.* 132:6-13), $^{32}$P-dCTP-labeled (specific activity>1× $10^9$ cpm/µg) probe for 12 hours at ca. 45° C. The filter is then washed twice for 30 minutes in 2×SSC, 0.5% SDS at least 55° C. (low stringency), more preferably at least 60° C. (medium stringency), more preferably at least 65° C. (medium/high stringency), more preferably at least 70° C. (high stringency), even more preferably at least 75° C. (very high stringency).

Molecules which hybridize to the oligonucleotide probe under these conditions are detected by exposure to x-ray film.

The following paragraphs describes how to prepare the transgenic plants of the invention, i.e. plants transformed so as to produce the enzymes as disclosed herein. Mainly maltogenic alpha-amylase is use as an examples but it is considered to be equally valid for the other enzymes mentioned herein, such as e.g. a beta-amylase.

Cloning a DNA Sequence Encoding a Maltogenic Alpha-amylase

The nucleotide sequence encoding the enzyme of the invention, such as the maltogenic alpha-amylase or beta-amylase, may be of any origin, including mammalian, plant and microbial origin and may be isolated from these sources by conventional methods.

Preferably, the nucleotide sequence is derived from a microorganism, such as a fungus, e.g. a yeast or a filamentous fungus, or a bacterium. The DNA sequence encoding a parent maltogenic alpha-amylase may be isolated from the cell producing the maltogenic alpha-amylase in question, using various methods well known in the art, for example, from the *Bacillus* strain NCIB 11837. First, a genomic DNA and/or cDNA library should be constructed using chromosomal DNA or messenger RNA from the organism that produces the maltogenic alpha-amylase to be studied. Then, if the amino acid sequence of the maltogenic alpha-amylase is known, homologous, labelled oligonucleotide probes may be synthesised and used to identify maltogenic alpha-amylase-encoding clones from a genomic library prepared from the organism in question. Alter-natively, a labelled oligonucleotide probe containing sequences homologous to a known maltogenic alpha-amylase gene could be used as a probe to identify maltogenic alpha amylase-encoding clones, using hybridization and washing conditions of lower stringency.

Another method for identifying maltogenic alpha amylase-encoding clones involves inserting fragments of genomic DNA into an expression vector, such as a plasmid, transforming maltogenic alpha-amylase negative bacteria with the resulting genomic DNA library, and then plating the transformed bacteria onto agar containing a substrate for maltogenic alpha-amylase, thereby allowing clones expressing maltogenic alpha-amylase activity to be identified.

Alternatively, the DNA sequence encoding the enzyme may be prepared synthetically by established standard methods, e.g. the phosphoroamidite method described by S. L. Beaucage and M. H. Caruthers (1981) or the method described by Matthes et al. (1984). In the phos-phoroamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin, wherein the fragments correspond to various parts of the entire DNA sequence, in accordance with techniques well known in the art. The DNA sequence may also be prepared by polymerase chain reaction (PCR) using specific primers, for instance as described in U.S. Pat. No. 4,683,202 or R. K. Saiki et al. (1988). See also WO 99/43794 disclosing how to make variants, e.g. by use of mutagenesis techniques known in the art.

Expression Constructs

In order to accomplish expression of the maltogenic alpha-amylase in seeds of the transgenic plant of the invention the nucleotide sequence encoding the amylase is inserted into an expression construct containing regulatory elements capable of directing the expression of the nucleotide sequence and, if necessary, to direct secretion of the gene product or targeting of the gene product to the seeds of the plant. Manipulation of nucleotide sequences using restriction endonucleases to cleave DNA molecules into fragments and DNA ligase enzymes to unite compatible fragments into a single DNA molecule with subsequent incorporation into a suitable plasmid, cosmid, or other transformation vector are well-known in the art.

In order for transcription to occur the nucleotide sequence encoding the maltogenic alpha-amulase is operably linked to a suitable promoter capable of mediating transcription in the plant in question. The promoter may be an inducible promoter or a constitutive promoter. Typically, an inducible promoter mediates transcription in a tissue-specific or growth-stage specific manner, whereas a constitutive promoter provides for sustained transcription in all cell tissues. An example of a suitable constitutive promoter useful for the present invention is the cauliflower mosaic virus 35 S promoter. Other constitutive promoters are transcription initiation sequences from the tumor-inducing plasmid (Ti) of Agrobacterium such as the octopine synthase, nopaline synthase, or mannopine synthase initiator.

Examples of suitable inducible promoters include a seed-specific promoter such as the promoter expressing α-amylase in wheat seeds (see Stefanov et al, Acta Biologica Hungarica Vol. 42, No. 4 pp. 323-330 (1991), a promoter of the gene encoding a rice seed storage protein such as glutelin, prolamin, globulin or albumin (Wu et al., Plant and Cell Physiology Vol. 39, No. 8 pp. 885-889 (1998)), a *Vicia faba* promoter from the legumin B4 and the unknown seed protein gene from *Vicia faba* described by Conrad U. et al, Journal of Plant Physiology Vol. 152, No. 6 pp. 708-711 (1998), the storage protein napA promoter from *Brassica napus*, or any other seed specific promoter known in the art, e.g. as described in WO 91/14772.

In order to increase the expression of the maltogenic alpha-amylase it is desirable that a promoter enhancer element is used. For instance, the promoter enhancer may be an intron which is placed between the promoter and the amylase gene. The intron may be one derived from a monocot or a dicot. For instance, the intron may be the first intron from the rice Waxy (Wx) gene (Li et al., Plant Science Vol. 108, No. 2, pp. 181-190 (1995)), the first intron from the maize Ubi1 (Ubiquitin) gene (Vain et al., Plant Cell Reports Vol. 15, No. 7 pp. 489-494 (1996)) or the first intron from the Act1 (actin) gene. As an example of a dicot intron the chsA intron (Vain et al. op cit.) is mentioned. Also, a seed specific enhancer may be used to increase the expression of the maltogenic alpha-amylase in seeds. An example of a seed specific enhancer is the one derived from the beta-phaseolin gene encoding the major seed storage protein of bean (Phaseolus vulgaris) disclosed by Vandergeest and Hall, Plant Molecular Biology Vol. 32, No. 4, pp. 579-588 (1996).

Also, the expression construct contains a terminator sequence to signal transcription termination of the maltogenic alpha-amylase gene such as the rbcS2' and the nos3' terminators.

To facilitate selection of successfully transformed plants, the expression construct should also include one or more selectable markers, e.g. an antibiotic resistance selection marker or a selection marker providing resistance to a herbicide. One widely used selection marker is the neomycin phosphotransferase gene (NPTII) which provides kanamycin resistance. Examples of other suitable markers include a marker providing a measurable enzyme activity, e.g. dihydrofolate reductase, luciferase, and β-glucoronidase (GUS). Phosphinothricin acetyl transferase may be used as a selection marker in combination with the herbicide basta or bialaphos.

Transgenic Plant Species

In the present context the term "transgenic plant" is intended to mean a plant which has been genetically modified to express a maltogenic alpha-amylase and progeny of such plant having retained the capability of producing a maltogenic alpha-amylase. The term also includes a part of such plant such as a leaf, seed, stem, any tissue from the plant, an organelle, a cell of the plant, etc.

Any transformable seed-producing plant species may be used for the present invention. Of particular interest is a monocotyledonous plant species, in particular crop or cereal plants such as wheat (*Triticum*, e.g. *aestivum*), barley (*Hordeum*, e.g. *vulgare*), oats, rye, rice, sorghum and corn (*Zea*, eg *mays*). In particular, wheat is preferred.

Transformation of Plants

The transgenic plant cell of the invention may be prepared by methods known in the art. The transformation method used will depend on the plant species to be transformed and can be selected from any of the transformation methods known in the art such as *Agrobacterium* mediated transformation (Zambryski et al., EMBO Journal 2, pp 2143-2150, 1993), particle bombardment(Vasil et al. 1991), electroporation (Fromm et al. 1986, Nature 319, pp 791-793), and virus mediated transformation. For transformation of monocots particle bombardment (i.e. biolistic transformation) of embryogenic cell lines or cultured embryos are preferred. In the following references disclosing methods for transforming different plants are mentioned together with the plant: Rice (Cristou et al. 1991, Bio/Technology 9, pp. 957-962), Maize (Gordon-Kamm et al. 1990, Plant Cell 2, pp. 603-618), Oat (Somers et al. 1992, Bio/Technology 10, pp 1589-1594), Wheat (Vasil et al. 1991, Bio/Technology 10, pp. 667-674, Weeks et al. 1993, Plant Physiology 102, pp. 1077-1084) and barley (Wan and Lemaux 1994, Plant Physiology 102, pp. 37-48, review Vasil 1994, Plant Mol. Biol. 25, pp 925-937).

More specifically, *Agrobacterium* mediated transformation is conveniently achieved as follows: A vector system carrying the maltogenic alpha-amylase is constructed. The vector system may comprise one vector, but it can comprise two vectors. In the case of two vectors the vector system is referred to as a binary vector system (Gynheung An et al. (1980), Binary Vectors, Plant Molecular Biology Manual A3, 1-19).

An *Agrobacterium* based plant transformation vector consists of replication origin(s) for both *E.coli* and *Agrobacterium* and a bacterial selection marker. A right and preferably also a left border from the Ti plasmid from *Agrobacterium tumefaciens* or from the Ri plasmid from *Agrobacterium rhizogens* is nessesary for the transformation of the plant. Between the borders the expression construct is placed which contains the maltogenic alpha-amylase gene and appropriate regulatory sequences such as promotor and terminator sequences. Additionally, a selection gene e.g. the neomycin phosphotransferase type II (NPTII) gene from transposon Tn5 and a reporter gene such as the GUS (betha-glucuronidase) gene is cloned between the borders. A disarmed *Agrobacterium* strain harboring a helper plasmid containing the virulens genes is transformed with the above vector. The transformed *Agrobacterium* strain is then used for plant transformation.

Industrial Processes

In principle, the seeds of the invention may be used in any industrial process for which purified maltogenic alpha-amylase or beta-amylase are normally used to catalyze a reaction between one or more substrate so as to produce the desired effects or products. Of particular interest for the present invention is the use of the seeds in the bread making process for improving the properties of a dough or a baked product. According to one embodiment of the present invention the seeds of the invention are used directly in the baking process without the need for first extracting and/or isolating the enzyme. For use in a baking process it is preferred that the seeds containing the maltogenic alpha-amylase or beta-amylase are milled so as to obtain a consistency suitable for baking.

According to one aspect of the invention the seeds, optionally in a ground form, are used for preparing a flour, in particular wheat flour. More specifically, the flour may be prepared by milling seeds of the invention containing a maltogenic alpha-amylase or a beta-amylase. The milling may be conducted in accordance with methods known in the art for preparing flour from seeds.

When a flour has been produced from seeds of the present invention the maltogenic alpha-amylase activity of the resulting flour is normally measured and the strength of the enzyme activity adjusted. For instance, if too much maltogenic alpha-amylase activity is present in the flour prepared from transgenic seeds of the invention the flour may be diluted with flour free from the maltogenic alpha-amylase. If too little maltogenic alpha-amylase activity is present in the flour additional activity may be added, e.g. in the form of an isolated maltogenic alpha-amylase, such as Novamyl® available from Novo Nordisk A/S. It follows, that the flour of the present invention may be prepared exclusively from transgenic seeds containing a maltogenic alpha-amylase or from a mixture of seeds which in addition to the transgenic seed of the invention contains non-transgenic seeds or seeds which otherwise do not contain the maltogenic alpha-amylase. The seeds of the invention preferably containes the maltogenic alpha-amylase in an amount which is effective to delay staling of a baked bread based on said seeds. One embodiment, the seed of the invention contains a measurable amount of the maltogenic alpha-amylase or the beta-amylase.

The flour of the invention may be is used in accordance with conventional techniques for the production of baked products, in particular bread products. The resulting baked product has an improved anti-staling effect, i.e. the baked product has a reduced rate of deterioration of quality parameters, e.g., softness and/or elasticity, during storage.

The maltogenic alpha-amylase, Novamyl®, has a very unique performance in bread making. Other thermostable α-amylases like BAN® or Termamyl® must be dosed very carefully in tight intervals, e.g. between 0.5-2 times of the optimum dosage in a given recipe. Otherwise the risk is high that there is either no effect (low dosage) or too high effect (high dosage). The latter will result in a gummy, non-elastic and sticky crumb, unsuited for eating. The maltogenic alpha-amylase as represented by Novamyl® does not have this problem, but can be dosed broadly. For instance, Novamyl® has a positive function on e.g. staling properties from a level of e.g. 200 MANU/kg flour to 5.000 MANU/kg, i.e. a much safer amylase in practical application than other α-amylases.

The term "baked product" is defined herein as any product prepared from a dough, either of a soft or a crisp character. Examples of baked products, whether of a white, light or dark type, which may be advantageously produced by the present invention are bread (in particular white, whole-meal or rye bread), typically in the form of loaves or rolls, French baguette-type bread, pasta, pita bread, tortillas, tacos, cakes, pancakes, biscuits, cookies, pie crusts, steamed bread, and crisp bread, and the like.

In terms of enzyme activity, the appropriate dosage of the maltogenic alpha-amylase for exerting a desirable improvement of dough and/or baked products, in particular improved anti-staling properties, will depend on the specific amylase and the amylase substrate in question. The skilled person may determine a suitable enzyme unit dosage on the basis of methods known in the art. Normally, a suitable dosage of the maltogenic alpha-amylase (as present in the flour) is in the range 200-5.000 MANU/kg flour.

Determination of Maltogenic Amylase in MANU

One Maltogenic Amylase Novo Unit (MANU) is the amount of enzyme which under standard will cleave one αmol maltotriose per minute. The standard conditions are 10 mg/ml maltotriose, 37° C., pH 5.0, 30 minutes reaction time. The pH dependence is found by repeating this measurement at the same conditions, but at different pH values.

The invention is further illustrated with reference to the following examples which are not intended to be in any way limiting to the scope of the invention as claimed.

EXAMPLES

Example 1

Plasmid Construction

The plant novamyl plasmid pNP110 is constructed from the plasmid pAHC25 (Christensen. A. H. Sharrock, R. A. and Quail, P. H. (1992) Plant Mol. Bio. 1 18 675-689) containing the UidA reporter gene encoding beta-glucuronidase (GUS) and the bar gene as selective marker encoding phosphinothricin acetyl transferase which inactivates phosphinothricin, the active component in the herbicides Basta and Bialaphos. Each driven by the maize ubi1 promoter and the first intron and terminated by the polyadenylation signal of nos3' gene from *Agrobacterium tumefaciens*. The Novamyl mature gene is amplified using the forward primer: FNP110: 5'-tcccccgggatgagcagttccgcaagcgtcaaa-340 and the reverse primer RNP110: 5'-cgatgagctcctagttttgc-cacgt-3' using the pDN452 plasmid as template (DIDER-ICHSEN B. and CHRISTIANSEN L. (1988) FEMS Microbiol. Lett. 56:53-60) under standard PCR conditions. The fragment of 2.0 Kb is digested with SmaI and SacI and ligated with the vector fragment of the plasmid pAHC25 digested with SmaI and SacI. The obtained plasmid designated pNP110 is used for the transformation experiments.

Transformation of Wheat

Plant Material:

Wheat (*Tritordeum aestivum* L.) plants are grown in greenhouses or in growth chambers in 16 h light (350 µmol $m^{-2}s^{-1}$)/8 h dark period at 16° C.

Wheat spikes are harvested when embryos are 1-2 mm. Caryopses are removed from the middle half of spikes 12 days after anthesis and surface sterilized for 10 min 5.25% sodium hypochlorite under stirring and finally washed twice in sterile $H_2O$. Immature embryos are dissected from caryopses under a stereomicroscope using a scalpel and transferred to Petri dishes containing MS medium with scutellum side up. Twenty immature embryos are placed side by side in an area of 1 cm×1 cm and are ready for bombardment the following day.

Culture Media:

Murashige and Skoog medium for immature embryos (MS):

4.3 g MS salts (Sigma M5524)

25 g Sucrose 100 mg Myo-inositol 500 mg Glutamin 100 mg Casein hydrolysate 5 g agarose $H_2O$ to 1 L and adjust pH to 5.8.

After autoclaving add 1 ml filter sterilized vitamin solution (10 mg thiamin, 50 mg nicotinic acid, 50 mg pyridoxine HCl and 200 mg glycine in 100 mL $H_2O$) and 1 mg 2,4-dichlorophenoxyacetic acid (2,4-D).

Selection Medium (MSS):

As MS without glutamine and casein hydrolysate, but with addition of 3 mg/L Bialaphos after autoclaving.

Shoot Induction Medium MSSI:

2.5 g MS salts; 15 g Sucrose; 50 mg Myo-inositol; 2.5 g agarose;

$H_2O$ to 1 l and adjust pH to 5.8.

After autoclaving add filter-sterilized 5 mg/l bialaphos and 0.5 ml/l vitamin solution as MS and 0.1 mg/l filter-sterilized BAP, 6-benzylaminopurine Root Induction Medium Standard MS-medium (Sigma M9274) with filter-sterilized 1 mg/l bialaphos Gold Coating:

6 mg gold particles are sterilized in 100 μl EtOH and vortexed for 3 min. After centrifugation at 10 K for 1 min and washed twice in $H_2O$ and finally the gold particles are resuspended in 100 μl $H_2O$.

15 μg pNP110 Plasmid DNA, 50 μl of 2.5 M CaCl2 and 20 μl of 0.1 M spermidine are mixed with 50 μl gold suspension during vortexing for 3 min and centrifuged at 500 rpm for 5 min at 4° C. Supernatant is removed and the pellet is resuspended in 500 μl EtOH and centrifuged 500 rpm for 5 min at 4° C.

Finally, the pellet is resuspended in 80 μl EtOH and 10 μl coated gold particles are transferred to macrocarriers soaked in 70% EtOH for 10 min and air dryed.

Bombardment of Embryos:

The bombardment chamber and the acceleration cylinder is sterilized by spraying with 70% EtOH and air dryed. The delivery pressure is set to 1300 psi.

The rupture disk (1100 psi) and the steel mesh are soaked in EtOH for 10 min and air dryed. Rupture disk is placed properly in the holder and is fastened tightly. The macrocarrier and the steel mesh in the assembly unit is placed properly in the chamber (level 2 from top). The Petri dish with immature embryos is placed properly in the chamber (level 4 from top). Vacuum is turn on and subsequently the pressure is turn on. at 1100 psi the rupture dish break and the DNA is bombarded into the immature embryos. The Petri dish is transferred to a growth chamber at 25° C. for 20 h without light.

The following day, the bombarded embryos are spread all over the area of the Petri dish containing MSS medium. After two to three transfers, one each second week, selected callus is transferred to shoot induction (MSSI) medium and transferred to a growth chamber with a 16 h light/8 h dark period. After two weeks green areas and shoot formation are visible. Only green-shoot-callus is transferred to new Petri dishes with MSSI medium or to tubes with root induction medium for two more weeks. Plant with roots in tubes are transferred to soil and placed in a greenhouse for three to four months and mature seeds are harvested.

Verification of Transgenic Wheat

Semipurification of Genomic DNA 0.25 g plant material in a eppendorf tube is chilled in $N_2$ and grinded.

500 μl phenol/chloroform 1:1 and 500 μl buffer (50 mM Tris-HCL, pH 9.0+150 mM LiCl, 5 mM EDTA, pH 8.0+5% SDS in H2O) is added with 10 μl RNAse (10 mg/ml).

Centrifuged 15000 rpm for 10 min

Topfase is transferred to a new eppendorf tube and 500 μl chloroform is added. Centrifuged 15000 rpm for 5 min and topfase is transferred to a new eppendorf tube and $^{1}/_{10}{}^{th}$ vol 3 M NaAc, pH 5.3 is added with 2 vol EtOH. The tube is placed on ice for 30-60 min.

Centrifuged 1500 rpm for 20 min.

Washed with 70% EtOH, spin 6 min and air dry for 15 min.

Resuspended in 30 $H_2O$ and check 3 μl in an agarose gel.

PCR Analysis:

To test for the presence of The novamyl gene in genomic DNA of transformed lines, 250 ng genomic DNA of each transgenic line is used as template in PCR using the forward primer FNP110: 5'-tccccegggatgagcagttccgcaagcgtcaaa-3' and the reverse primer RNP110: 5'-cgatgagctcctagttttgc-cacgt-3'. Standard PCR conditions are used with 40 cycles of 1 min at 94° C., 1 min at 61° C., 2 min 72° C.

Novamyl Positive plant lines showed a band of 2.0 kb, whereas non transformed plants showed no fragments of 2.0 kb Example 2

The nucleotide sequence encoding Novamyl (SEQ ID NO: 1) is operably linked to the wheat promoter expressing α-amylase in wheat seeds as described in "Promoter and genotype dependent transient expression of a reporter gene in plant protoplasts."; Stefanov I; llubaev S; Feher A; Margoczi K; Dudits D; Acta Biologica Hungarica Vol. 42, No. 4 pp. 323-330 (1991 The resulting DNA construct is inserted into a plasmid containing suitable regulatory elements and a selection marker, such as described in Example 1.

Protoplasts are isolated from wheat cell lines as described in ("Culture of and fertile plant-regeneration from regenerable embryogenic suspension cell-derived protoplasts of wheat (triticum-aestivum I)"; Ahmed, K Z; Sagi, F; PLANT CELL REPORTS Vol. 12, pp. 175-179 (1993).

The nucloetide construct containing the maltogenic alpha-amylase coding sequence is inserted into wheat protoplast cells via PEG treatment as described in "Factors affecting transient expression of vector constructs in wheat protoplasts."; Ahmed K Z; Omirulleh S ; Sagi F; Dudits D; Acta Biologica Hungarica Vol. 48, No. 2 pp. 209-220 (1997). The resulting protoplast is regenerated into a wheat plant as described in "Fertile wheat (*Triticum aestivum* L.) regenerants from protoplasts of embryogenic suspension culture."; Pauk J; Kertesz Z; Jenes B; Purnhauser L; Manninen O; Pulli S; Barbas Z; Dudits D; Plant Cell Tissue and Organ Culture Vol. 38, No. 1 pp. 1-10 (1994). The seeds are harvested, and multiplied and used for producing transgenic wheat plant expressing Novamyl in its seeds.

Example 3

The wheat seeds are milled in accordance with conventional techniques for the preparation of wheat flour. Optionally, the wheat is allowed to malt to a predetermined degree before milling. This will allow a greater expression of the bacterial enzyme. The Novamyl content of the flour is determined in MANU: One MANU (Maltogenic Amylase Novo Unit) is defined as the amount of enzyme required to release one mmol of maltose per minute at a concentration of 10 mg of maltotriose (Sigma M 8378) substrate per ml of 0.1 M citrate buffer, pH 5.0 at 37° C. for 30 minutes. If needed the content of Novamyl in the flour is adjusted as discussed above in the Detailed Description so as to result in a Novamyl content per kg of flour in the range of 200-5000 MANU/kg of flour.

Example 4

A baking trial is carried out. The transformed flour is compared to the original un-transformed wheat "sort". The optimum water absorption is determined on a Farinograph (AACC method The Farinograph Handbook, 3rd Edition, 1984, AACC, Edited by Bert L. D'Appolonia and Wallace H. Kunerth, ISBN 0-913250-37-6).

Preparation of White Bread (I)

The straight-dough bread-making method may be used according to AACC Method 10-10B (in Approved Methods of the American Association of Cereal Chemists, Ninth Edition, March 1995; AACC, St. Paul Minn., USA).

Basic Recipe

| | |
|---|---|
| Wheat flour | 100% |
| Salt | 1.5% |
| Yeast (fresh) | 5.3% |
| Sugar | 6.0% |
| Shortening | 3.0% |
| Water | optimum |

All percentages are by weight relative to the wheat flour.

Procedure
1. Dough mixing (Hobart mixer):
 The mixing time and speed should be determined by the skilled baker so as to obtain an optimum dough consistency under the testing conditions used.
2. 1st punch (e.g., 52 minutes after start)
3. 2nd punch (e.g., 25 minutes later)
4. Molding and panning (e.g., 13 minutes later).
5. Proofing to desired height (e.g., 33 minutes at 32° C., 82% RH)
5. Baking (e.g., at 215° C. for 24 minutes)

Preparation of White Bread (II):

The sponge-dough bread-making method may be used according to AACC Method 10-11 (in Approved Methods of the American Association of Cereal Chemists, Ninth Edition, March 1995; MCC, St. Paul Minn., USA).

Basic Recipe for Sponge

| | |
|---|---|
| Wheat flour | 60% |
| Yeast (compressed) | 36% |
| Yeast Food | 2% |
| Water | 36% |

All percentages are by weight relative to the wheat flour.

Procedure
1. Add water to compressed yeast
2. Add yeast food in dry form with flour
3. Mix sponge (Hobart A-120; Hobart Corp., Troy Ohio, USA):

0.5 minute at $1^{st}$ speed
 1 minute at $2^{nd}$ speed
 The mixing time may be adjusted so as to obtain an optimum dough consistency under the testing conditions used.
4. Ferment in a fermentation cabinet: 4 hours at 30° C., 85% RH Basic Recipe for Dough

| | |
|---|---|
| Wheat flour | 40% |
| Water | 24% |
| Sugar | 5% |
| Shortening | 3% |
| Salt | 2% |

All percentages are by weight relative to the wheat flour.

Procedure
1. Add dough ingredients; begin mixer ($1^{st}$ speed)
2. Add sponge in three approximately equal portions at 15, 25, and 35 seconds mixing time; total mixing time: 1 minute
3. At $2^{nd}$ speed, mix to obtain an optimum dough consistency
4. Ferment in a fermentation cabinet: 30 minutes at 30° C., 85% RH
5. Intermediate proof: 12-15 minutes in fermentation cabinet
6. Mold and final proof at 35.5° C., 92% RH
7. Bake: 25 minutes at 218° C.

Example 5

Evaluation of Staling Properties of Bread:

The degree of staling is determined on bread, e.g., on day 1, 3, 7 and 9 after baking. Evaluation of staleness and texture can be done according to AACC method 74-09. The principles for determination of softness and elasticity of bread crumb are as follows:
1. A slice of bread is compressed with a constant speed in a texture analyser, measuring the force for compression in g.
2. The softness of the crumb is measured as the force at 25% compression.
3. The force at 40% compression (P2) and after keeping 40% compression constant for 30 seconds (P3) is measured. The ratio (P3/P2) is the elasticity of the crumb.

The invention claimed is:

1. A transgenic cereal plant cell comprising a nucleotide sequence encoding a maltogenic alpha-amylase; wherein the maltogenic alpha-amylase has an amino acid sequence which has at least 85% identity to amino acids 34-719 of SEQ ID NO: 2.

2. The plant cell according to claim 1, wherein the plant cell is a wheat plant cell.

3. The plant cell according to claim 1, wherein the maltogenic alpha-amylase has the amino acid sequence of amino acids 34-719 of SEQ ID NO:2.

4. The plant cell according to claim 1, wherein said wherein the nucleotide sequence is operably linked to a seed specific promoter.

5. The plant cell according to claim 1, wherein the nucleotide sequence encoding the maltogenic alpha-amylase is derived from a microorganism.

6. The plant cell according to claim 1, wherein the nucleotide sequence encoding the maltogenic alpha-amylase is derived from the *Bacillus* strain NCIB 11837.

7. A transgenic cereal plant regenerated from a plant cell of claim 1 or the progeny of the plant, wherein the plant and the progeny of the plant are capable of expressing maltogenic alpha-amylase in the seeds of the plant or the progeny of the plant.

8. A transgenic cereal plant comprising a nucleotide sequence encoding a maltogenic alpha-amylase; wherein the maltogenic alpha-amylase has an amino acid sequence which has at least 85% identity to amino acids 34-719 of SEQ ID NO: 2.

9. The plant according to claim 8 which is a wheat plant.

10. The plant according to claim 8, wherein the maltogenic amylase is a maltogenic alpha-amylase having the amino acid sequence of amino acids 34-719 of SEQ ID NO: 2.

11. A seed of the cereal plant of claim 8, wherein the seed includes maltogenic alpha-amylase in an amount effective to delay staling of bread baked from the seed.

12. A transgenic cereal seed comprising a maltogenic alpha-amylase in an amount effective to delay staling of bread baked from the seed; wherein the maltogenic alpha-amylase has an amino acid sequence which has at least 85% identity to amino acids 34-719 of SEQ ID NO: 2.

13. The seed of claim 12, wherein the maltogenic alpha-amylase is a maltogenic alpha-amylase having the amino acid sequence of amino acids 34-719 of SEQ ID NO: 2.

14. The seed of claim 12, wherein the seed is a wheat seed.

15. A method for preparing a baked product, comprising the steps of:
   i) preparing a dough from flour obtained from cereal seed, said seed comprising a maltogenic alpha-amylase, wherein the maltogenic alpha-amylase has an amino acid sequence which has at least 85% identity to amino acids 34-719 of SEQ ID NO: 2; and [wherein the maltogenic alpha amylase is a maltogenic alpha amylase having:
   (a) the amino acid sequence shown in SEQ ID NO: 2;
   (b) the amino sequence acid sequence of amino acids 1-686 of SEQ ID NO: 1;
   (c) an amino acid sequence which has at least 85% identity to SEQ ID NO: 2; or
   (d) an amino acid sequence which has at least 85% identity to the amino acid sequence set forth in amino acids 1-686 of SEQ ID NO: 1; and]
   ii) baking the dough to obtain a baked product.

16. The method according to claim 15, wherein the seed includes the maltogenic alpha-amylase in an amount effective to delay staling of the bread product.

17. The transgenic cereal plant cell of claim 1, wherein the maltogenic alpha-amylase has an amino acid sequence which has at least 90% identity to amino adds 34-719 of SEQ ID NO: 2.

18. The transgenic cereal plant cell of claim 1, wherein the maltogenic alpha-amylase has an amino acid sequence which has at least 95% identity to amino acids 34-719 of SEQ ID NO: 2.

19. The transgenic cereal plant cell of claim 1, wherein the maltogenic alpha-amylase has an amino acid sequence which has at least 97% identity to amino acids 34-719 of SEQ ID NO: 2.

20. The transgenic cereal plant cell of claim 1, wherein the maltogenic alpha-amylase has an amino acid sequence which has at least 98% identity to amino acids 34-719 of SEQ ID NO: 2.

21. The transgenic cereal plant cell of claim 1, wherein the maltogenic alpha-amylase has an amino acid sequence which has at least 99% identity to amino acids 34-719 of SEQ ID NO: 2.

* * * * *